United States Patent [19]

Arthur et al.

[11] Patent Number: 5,705,331

[45] Date of Patent: *Jan. 6, 1998

[54] HIV NUCLEOCAPSID PROTEIN CAPTURE ASSAY AND METHOD OF USE

[75] Inventors: Larry O. Arthur, Walkersville; Louis E. Henderson, Mt. Airy, both of Md.

[73] Assignee: The United States of America as represented by the Secretary Department of Health & Human Services, Washington, D.C.

[*] Notice: The portion of the term of this patent subsequent to Oct. 31, 2002, has been disclaimed.

[21] Appl. No.: 485,833

[22] Filed: Jun. 7, 1995

Related U.S. Application Data

[63] Continuation of Ser. No. 967,658, Oct. 28, 1992, Pat. No. 5,462,852.
[51] Int. Cl.⁶ .................................................. C12Q 1/70
[52] U.S. Cl. ...................... 435/5; 435/7.1; 435/7.72; 435/7.9; 435/7.92; 435/7.94; 435/794; 435/975; 530/388.3; 530/388.35
[58] Field of Search .................. 435/5, 7.1, 7.72, 435/7.9, 7.92, 7.94, 974, 975; 530/350, 388.3, 388.35, 806, 826

[56] References Cited

U.S. PATENT DOCUMENTS 5,462,852 10/1995 Arthur et al. ............................ 435/5

OTHER PUBLICATIONS

Louis E. Henderson et al., "Gag Proteins of the Highly Replicative MN Strain of Human Immunodeficiency Virus Type 1: Posttranslational Modifications, Proteolytic Processings, and Complete Amino Acid Sequences," *Journal of Virology*, 66(4):1856–1865 (Apr. 1992).

Sharon A. Cassol et al., "Diagnosis of Vertical HIV–1 Transmission Using the Polymerase Chain Reaction and Dried Blood Spot Specimens," *Journal of Acquired Immune Deficiency Syndromes*, 5:113–119 (1992).

Judith N. Peisen, "Development and Application of Immunoassays to Detect and Characterize p7 Immunogenicity in HIV–1 Infected Populations," *Master Thesis in Biomedical Science in the Graduate School of Hood College*, pp. 17–25, 96–117 (Nov. 16, 1991).

Maadhava Ellaurie et al., "Correlation of Serum Antigen and Antibody Concentration with Clinical Features in HIV Infection," *Archives of Disease in Childhood*, 66(2):200–203 (Feb. 1991).

Robert J. Gorelick et al., "Noninfectious Human Immunodeficiency Virus Type 1 Mutants Deficient in Genomic RNA," *Journal of Virology*, 64(7):3207–3211 (Jul. 1990).

*Primary Examiner*—Christine M. Nucker
*Assistant Examiner*—Jeffrey Stucker
*Attorney, Agent, or Firm*—Needle & Rosenberg, P.C.

[57] ABSTRACT

An antigen capture method, and an antigen capture assay diagnostic kit, for detecting the presence or concentration of HIV in a biological sample without interference from antigen-antibody immune complexes is provided. The lysate of a biological sample obtained from an animal is contacted with a detectable mount of an antibody specifically reactive with the nucleocapsid p7 antigen or an immunoreactive fragment of the p7 antigen for a time and under conditions sufficient for p7 antigen contained in the lysate to form a p7-antibody complex. The presence or concentration of this p7-antibody complex is determined to detect or quantitate the presence of HIV in the biological sample. Uses of this assay and method include detecting the presence of HIV infection in an infant born to an HIV-infected mother, monitoring the progression of HIV infection, and evaluating the effectiveness of an anti-HIV treatment administered to an animal, such as a human. Purified antibodies specifically reactive with an immunoreactive epitope specific to p7 or an immunoreactive fragment of p7 are also provided as well as an antigen capture method for detecting the presence of a lentivirus in a biological sample involving the nucleocapsid protein of the lentivirus.

13 Claims, 2 Drawing Sheets

HIV NUCLEOCAPSID PROTEIN CAPTURE ASSAY AND METHOD OF USE

This application is a continuation of application Ser. No. 07/967,658, filed Oct. 28, 1992 issued on Oct. 31, 1995 as U.S. Pat. No. 5,462,852.

BACKGROUND OF THE INVENTION

The instant invention relates to the detection of Human Immunodeficiency Virus (HIV) in a biological sample containing bodily fluids, such as serum and plasma, tissues, or cell culture fluid and the like, utilizing an immunological capture assay involving the HIV nucleocapsid protein, p7, or an immunoreactive fragment of p7. Uses for this invention include determining the prognosis of disease in an HIV-infected person, monitoring the effectiveness of antiviral treatment, detecting HIV-infection in infants born to HIV-infected mothers, and detecting and quantitating HIV in laboratory experiments (i.e., virus production, infectivity assays, neutralization assays, drug effectiveness assays, etc.).

Surrogate markers of AIDS progression are needed to establish the requirement and effectiveness of any particular antiviral treatment. Several surrogate markers for disease progression have been studied, including measurement of absolute numbers of CD4+cells, β-2 microglobulin plasma concentrations, serum neoptrin levels, amounts of infectious virus in PBLs, HIV-1 antigen levels in plasma and decrease or disappearance of antibodies to p24 [Jacobsen et al, *British Medical Journal*, 302:73 (1991) and Bagasra et al., *N. Eng. J. Med.*, 326:1385–91 (1992)]. Difficulties exist with most of these markers when used to predict disease progression or to detect HIV infection, such as in infants born to HIV-infected mothers. Although there is a direct correlation between absolute numbers of CD4 positive T-cells and opportunistic infections resulting in death, CD4 cell counts are not satisfactory as disease progression markers because the slope of their decrease is low in most seropositive individuals [Andrieu, *Clin. Exp. Immunol.*, 73:1 (1988)].

However, a direct correlation has been reported between the levels of infectious HIV-1 in plasma from infected individuals and AIDS progression, emphasizing the need to quantitatively determine HIV-1 in plasma of infected persons [Michael et al., *J. Vir.*, 66:310–316 (1992); Katzenstein et al., *J. Acquired. Imm. Deficiency Syndromes*, 5:107–112 (1992) and Henrard et al., *AIDS Res. & Human Retroviruses*, 8:47 (1992)]. Increased concentrations of HIV-1 in plasma or serum is usually measured by (1) tissue culture assays to detect infectious virus (2) polymerase chain reaction (PCR) to detect the viral genomic RNA (3) antigen capture assays using the capsid antigen, p24, or matrix antigen, p17, to detect HIV-1 proteins. However, viral isolation and polymerase chain reaction assays are laborious, time consuming and require a very high level of technical competence. Detection of HIV-1 in plasma by p24 and p17 capture assays is not reliable because antibodies to these proteins in the patient interfere with detection in the capture assays [Vjhelyi et al., *AIDS*, 1:161–165 (1987) and Nishanian et al, *J. Inf. Diseases*, 962:21–28 (1990)]. Consequently p24 cannot be detected in many of the asymptomatic individuals and AIDS patients. Additionally, because of interference with maternal antibodies, p24 antigen capture assays are insensitive to detecting HIV infection in infants born of HIV-infected mothers [Cassol, et al., *J. Acquired Imm. Deficiency Syndromes*, 5:113–119 (1992)].

The importance of antigen capture assays to identify viremia is underscored by the development of various procedures employed to detect antigen in the presence of antibodies. These procedures include methods to disrupt immune complexes between anti-p24 and p24, [Mathiesen et al, *J. Vir. Methods*, 22:143–148 (1988); Fiscus et al., *J. Inf. Diseases*, 164:765–9 (1991) and Kestens et al., *J. Vir. Methods*, 31:67–76 (1991)], measurement of the quantitative capacity for serum to complex with p24 [Crosxon et al, *AIDS Research & Human Retroviruses*, 6:455 (1990)] and use of antibodies to HIV-1 envelope antigens to capture the virus with subsequent detection by PCR [Henrard et al., *AIDS Research & Human Retroviruses*, 8:47 (1992)]. These more complicated procedures are limited to use in well-equipped laboratories and may suffer from sensitivity and reproducibility problems.

However, a simple, rapid assay to quantitate HIV-1 viremia would be valuable, for instance, as (1) a prognostic indicator to determine when an HIV-infected person is progressing to AIDS, to determine if an individual is infected with HIV, and to compliment the current antibody-based assays to detect HIV infection, (2) in monitoring the effectiveness of anti-viral treatment (or effectiveness of a new potential anti-HIV drug), (3) to determine if a vaccinated individual (i.e., a person that has been immunized with HIV, developed antibodies to HIV proteins and would consequently score positive in the antibody-based assays to detect HIV infection) was infected with HIV, (4) in determining if infants born to HIV-infected mothers are infected with HIV to allow early intervention and (5) as a method to detect and quantitate HIV in assays in clinical and research laboratories (e.g., isolation of HIV from PBMCs, propagation of HIV in cells, neutralization assays, drug-sensitivity assays, etc.) For instance, there is currently no simple test to predict or to confirm the presence of virus in an infant born to an HIV-1 infected mother. Neonatal IgM antibodies are often absent, p24 capture assays are insensitive and isolation of virus is slow, tedious, and requires specialized tissue culture facilities. However, detection is needed to permit early and effective clinical management of infected children and to reliably identify uninfected children. Thus, there exists a need for a surrogate marker for detecting HIV viremia and for a rapid, accurate assay for measurement of the levels of infectious HIV in the plasma, serum or other body fluids such as saliva and or cells such as PBMC's of infected individuals.

Furthermore, similar problems exist for lentiviruses other than HIV-1. Thus, there also exists a need for an accurate method for detecting and quantitating levels of HIV-2, SIV and other related lentivruses in biological samples obtained from animals.

Throughout this application, various publications are referenced. The disclosures of these publications in their entireties are hereby incorporated by reference into this application in order to more fully describe the state of the art to which this invention pertains.

SUMMARY OF THE INVENTION

This invention relates to an antigen capture method for detecting the presence of HIV in a biological sample, such as bodily fluid, tissue, or cell culture fluid obtained from an animal, without interference from antigen-antibody immune complexes, comprising the steps of contacting a lysate of the biological sample with a detectable amount of an antibody specifically reactive with the nucleocapsid p7 antigen or an immunoreactive fragment of the p7 antigen for a time and under conditions sufficient for p7 antigen contained in the lysate to form a p7-antibody complex and determining the presence, and optionally the concentration, of the p7-antibody complex, thereby detecting the presence, and optionally the extent, of HIV in the biological sample. Further, this invention provides an antigen capture assay diagnostic kit for the detection of the presence or amount of p7 comprising an antibody, polyclonal or monoclonal, specifically reactive with the p7 antigen or an immunoreactive fragment of the p7 antigen and means for detecting the formation of immune complexes between p7 and the antibody specifically reactive with the p7 antigen or an immunoreactive fragment of the p7 antigen. This invention also provides a purified antibody specifically reactive with an immunoreactive epitope specific to p7 or an immunoreactive fragment of p7. Uses of this method and assay include detection of the presence or absence of HIV infection in an infant born to an HIV-infected mother.

Furthermore, by obtaining biological samples from the animal a multiplicity of times spaced over a period of time and analyzing these samples according to this method and assay, this invention provides for the monitoring of the progression of HIV infection in an animal, especially a human. That is, an increase in the concentration of p7 in a biological sample obtained later in the period of time compared to the concentration of p7 from an earlier sample correlates with increased progression of HIV infection. In particular, the increase in the concentration of p7 can indicate the transition from asymptomatic HIV infection to the development of AIDS.

Additionally, the effectiveness of an anti-HIV treatment administered to an animal can be evaluated using this method and assay. That is, both an initial biological sample taken prior to administration of the anti-HIV treatment and a later biological sample taken at least one time subsequent to the administration of the anti-HIV treatment can be obtained from an animal. The concentrations of p7 in the initial and later samples can be determined using the method and assay of this invention and compared. A decrease of the concentration of p7 in the later sample correlates with a decreased level of HIV viremia.

This invention also provides an antigen capture method and assay for detecting the presence of a lentivirus in a biological sample, comprising contacting a lysate of the biological sample with a detectable amount of an antibody specifically reactive with the nucleocapsid protein of the lentivirus or an immunoreactive fragment of the nucleocapsid protein for a time and under conditions sufficient for nucleocapsid protein contained in the lysate to form a nucleocapsid protein-antibody complex and determining the presence of the nucleocapsid protein-antibody complex, thereby detecting the presence of the lentivirus in the biological sample. Typically, the lentivirus can be HIV-1, HIV-2, SIV, bovine immunodeficiency virus, feline immunodeficiency virus, equine infectious anemia virus, caprine arthritis encephalitis virus or visna virus.

Thus, it is an object of this invention to provide a sensitive antigen capture assay capable of measuring the level of a prognostic marker of HIV infection. In particular, this invention provides an antigen capture assay which includes a purified antibody to p7 or to an immunoreactive fragment of p7, such as a polyclonal or monoclonal antibody. This p7 antigen capture assay has the distinct advantage over other HIV antigen capture assays in that it does not suffer from interference with antigen/antibody complexes. Furthermore, use of p7 to detect the presence of virus is feasible since p7 is present in HIV in equal molar quantities to p24 and p17.

It is also an object of this invention to provide an antigen capture assay capable of determining if an individual is infected with HIV. Uses of this assay include complimenting other antibody-based assays to detect HIV infection and determining whether an individual that has been vaccinated against HIV (i.e., immunized with HIV) is infected with HIV.

It is a further object of this invention to provide an antigen capture assay, and an associated method of using the assay, which is capable of monitoring the progression of HIV infection, particularly in asymptomatic subjects. Thus, it is an object to provide a method and assay that allow identification of the majority of individuals who will rapidly progress to AIDS. Additionally, it is an object of this invention to provide a method of predicting or confirming the presence of virus in an infant born to an HIV-infected mother using the assay of this invention. Further, this assay can be used to detect the presence of virus prior to the development of antibodies to HIV.

A particular object of this invention is to provide a method of evaluating antiviral treatments. In particular, because the assay of this invention is able to measure the concentration of p7 in serum or plasma, which correlates with the level of infectious HIV in serum, plasma or the like from infected individuals and AIDS progression, this invention provides a surrogate marker sensitive to antiviral treatment. As such, measurement of p7 levels as taught in this invention allows screening of potential anti-HIV treatments for determination of effective anti-HIV regimens or to monitor the progress of a particular anti-HIV treatment. This p7 capture assay can also be used to detect and quantitate the virus in PBMCs and other bodily fluids (i.e., saliva, urine, milk, secretions, etc.)

An additional object of this invention is to provide a method for detecting and quantitating HIV-1 in clinical and research laboratories such as propagation in cell culture, isolation from PBMCs, neutralization assays, drug-sensitivity assays, etc. Furthermore, this invention provides antigen capture assays, and methods for their use, involving the nucleocapsid proteins from other lentiviruses, such as SIV, HIV-2, bovine immunodeficiency virus (BIV), feline immunodeficiency virus (FIV), equine infectious anemia virus (EIAV), caprine arthritis encephalitis virus (CAEV) and visna virus.

DETAILED DESCRIPTION OF THE INVENTION

Figure 1:
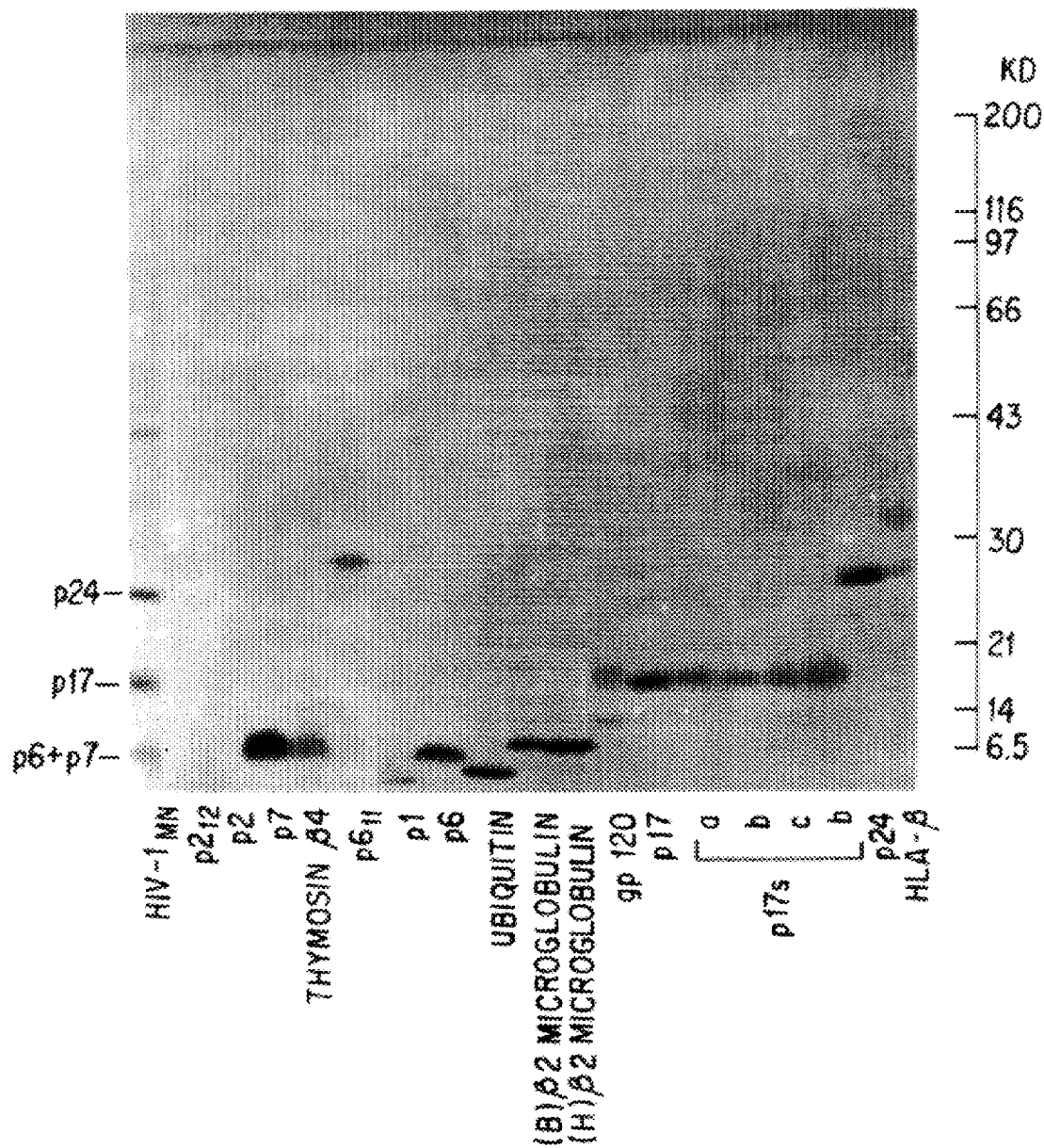
FIG. 1 shows Coomassie blue-stained gel of purified proteins isolated from HIV-1$_{MN}$. The purified proteins were analyzed by SDS-PAGE on 6 to 18% polyacrylamide gradient gels and detected by staining with Coomassie brilliant blue R-250. Lane HIV-1$_{MN}$ contained whole disrupted virus, and lanes p7, p1, p6, p24, and p17a–p17e contained approximately 3 to 5 µg of purified protein.

As used herein, the term "p7" refers to the purified nucleocapsid protein of HIV derived from the Gag precursor protein, such as the nucleocapsid protein of human immunodeficiency virus type 1 (HIV-1) and the various strains of HIV, such as HIV-1$_{MN}$. The term "immunoreactive fragment of p7" refers a fragment of p7 such that a purified antibody to the immunoreactive fragment is specifically reactive with an immunoreactive epitope specific to p7. As used herein, the term "nucleocapsid protein" encompasses the nucleocapsid proteins found in lentiviruses such as, HIV-1, HIV-2, SIV, bovine immunodeficiency virus (BIV), feline immunodeficiency virus (FIV), equine infectious anemia virus (EIAV), caprine arthritis encephalitis virus (CAEV) and visna virus. An "immunoreactive fragment of a nucleocapsid protein" refers to a fragment of the nucleocapsid protein such that a purified antibody to the immunoreactive fragment is specifically reactive with an immunoreactive epitope specific to the nucleocapsid protein. As used herein, "purified" means the protein (antigen) or antibody is sufficiently free of contaminants or cell components to distinguish it from the contaminants or cell components.

A fragment of p7 or a fragment of a nucleocapsid protein can be purified from the p7 antigen or the nucleocapsid protein, respectively, by chemical or mechanical disruption or can be synthesized, using standard techniques. The purified fragments of p7 (or the nucleocapsid protein) thus obtained can be tested to determine their antigenicity and specificity by methods known to one skilled in the art, such as by attempting to provoke antibodies according to the procedures given in Example 2 below and ascertaining the specificity of the immunogenic fragment by testing, for example, sera from animals inoculated with the fragment for cross reactivity with other closely related viruses. An immunoreactive epitope specific to p7 is defined as an amino acid sequence of at least about 5 consecutive amino acids derived from the purified p7 antigen and having immunoreactivity for an antibody specific to the p7 antigen. Immunoreactive fragments of p7 include, for instance, the amino terminus of p7, such as the amino acids which comprise the first zinc finger of p7, and the carboxy terminus of p7, such as the amino acids which comprise the second zinc finger of p7. Similarly, an immunoreactive epitope specific to a nucleocapsid protein is defined as an amino acid sequence of at least about 5 consecutive amino acids derived from the purified nucleocapsid protein and having immunoreactivity for an antibody specific to the nucleocapsid protein.

The biological samples which can be tested by the assay of this invention include bodily fluids, tissues, cell culture fluid and the like. Thus, samples include any bodily fluid which would contain the p7 antigen (or the nucleocapsid protein) or a cell containing the antigen, such as PBMC's blood, plasma, serum, saliva and urine. Other possible examples of body fluids include sputum, mucus and the like. The biological samples can be obtained, using methods standard in the art, from an animal such as a human (particularly for HIV) or a primate (particularly for SIV).

Ideally, an HIV-1 antigen used in a capture assay should be synthesized in the same molar quantities as p24 and not stimulate an efficient antibody response in HIV-1 infected persons. HIV-1 p24 and p17, along with the nucleocapsid protein p7, p6 and two linker proteins p1 and p2 are proteolytic products of a gag-coded precursor protein [Henderson et al, *J. Vir.*, 66:1852–1865 (1992). This Gag precursor protein is packaged in the virus prior to processing and, therefore, all Gag proteins are found in the virus in equal molar quantities.

Following purification of all the Gag proteins of HIV-1, these proteins were used for antisera generation. Animals immunized with linker proteins, p1 and p2, did not develop antibodies to the proteins and, thus, could not be initially used in development of capture assays. Also, p6 appears to be the most variable Gag protein among HIV-1 isolates and consequently may not detect all HIV-1 isolates. This instant invention reports the unexpected discovery that antibodies to the nucleocapsid protein, p7 are not detected in serum samples from HIV-1 infected persons (using an ELISA) yet can be raised in appropriate animal systems. This lack of antibodies to p7 in HIV-infected individuals, and, thus, the lack of interfering immune complexes such as those found with p24 and p17, coupled with the fact that p7 is found in equal molar quantities to p24 in the virus, makes p7 an ideal candidate for antigen capture assay development to detect HIV-1 viremia. The instant invention provides for a p7 antigen capture assay and detection of antigenemia in biological samples sera from HIV-1 infected persons using this assay. In particular, the instant invention provides a method of detecting the presence of HIV in a biological sample that may contain HIV by contacting a purified antibody specifically reactive with the p7 antigen and detecting the reaction of the antibody with the antigen. Furthermore, this invention provides for an antigen capture assay involving the nucleocapsid protein in other lentiviruses such as HIV-2, SIV, BIV, EIAV, CAEV and visna virus as well as the detection of antigenemia in biological samples from animals infected with these viruses.

A purified antibody specifically reactive with an immunoreactive epitope specific to p7 or an immunoreactive fragment of p7 is also provided. Similarly, this invention provides for antibodies specifically reactive with the nucleocapsid protein or an immunogenic fragment of the nucleocapsid protein. The term "reactive" means capable of binding or otherwise associating nonrandomly with the antigen. "Specifically" immunoreactive as used herein denotes the reactivity of an antibody for the p7 antigen (or the nucleocapsid protein) or an epitope of the p7 antigen (amino acid, protein, peptide or fragment) or nucleocapsid protein such that it does not cross react substantially with other antigens. As contemplated herein, the term "purified antibody" includes polyclonal antibodies, monoclonal antibodies or any ligand which binds p7 (or the nucleocapsid protein), for example, a fragment of an antibody, such as Fab or F(ab)$^2$, or another reagent that has specific reactivity with p7. A "detectable amount" of a purified antibody specifically reactive with p7 or an immunoreactive fragment of p7 refers to that quantity required to react with all the p7 or immunoreactive fragment of p7 present. A "detectable amount" with respect to antibodies specifically reactive with the nucleocapsid protein or its fragments is defined similarly. The antibody can be labeled with a detectable moiety or attached to a solid support, such as described below. Additional antibodies can be made by the procedures set forth in the Examples or by standard procedures, such as those disclosed in Harlow and Lane, *Antibodies; A Laboratory Manual*, Cold Spring Harbor Laboratory, Cold Spring Harbor, N.Y. (1988). Briefly, purified antigen or immunoreactive fragments thereof can be injected into an animal in an amount and in intervals sufficient to elicit an immune response. Antibodies can either be purified directly, or spleen cells can be obtained from the animal. The cells are then fused with an immortal cell line and screened for antibody secretion.

The present invention further provides a kit for detecting the antigen. Particularly, the kit can detect the presence of an antigen specifically reactive with the antibody or an immunoreactive fragment thereof. The kit can include an antibody bound to a substrate, a secondary antibody reactive with the antigen and a reagent for detecting a reaction of the secondary antibody with the antigen. Such a kit can be an antigen capture assay kit, such as an ELISA kit, and can comprise the substrate, primary and secondary antibodies when appropriate, and any other necessary reagents such as detectable moieties, enzyme substrates and color reagents as described above. The antigen capture diagnostic kit can, alternatively, be an immunoblot kit generally comprising the components and reagents described herein. The particular reagents and other components included in the diagnostic kits of the present invention can be selected from those available in the art in accord with the specific diagnostic method practiced in the kit. Such kits can be used to detect the antigen in biological samples, such as tissue and bodily fluid obtained from a subject.

The assay of the instant invention can be used to detect the presence and amount of HIV in a biological sample, without interference from antigen-antibody immune complexes, by contacting a lysate of the biological sample with a detectable amount of an antibody specifically reactive with the p7 antigen or an immunoreactive fragment of the p7 antigen for a time and under conditions sufficient for p7 antigen contained in the lysate to form a p7-antibody complex and determining the presence and amount of the p7-antibody complex to detect the presence and amount of HIV in the biological sample. The antibody can be immobilized and excess antibody that is not bound to p7 can be removed to allow binding of a secondary antibody, which is labeled with a detectable moiety, to the p7-antibody complex. The detectable moiety can then be used to measure the presence and amount of p7 in the biological sample and, thus, measure the presence and amount of HIV in the biological sample. The biological sample may include a bodily fluid, tissue or cell culture fluid, preferably blood, plasma or serum. For instance, the biological sample may be plasma or serum obtained from an infant born to an HIV-infected mother. Thus, the instant invention provides a simple test to predict or to confirm the presence of virus in the infant, even in the presence of antibodies derived from the mother's infection, to allow early and effective clinical management of infected children and to identify those that are not infected.

Further, this method can be used to detect infection early during the course of HIV infection, such as prior to antibody development. At this stage, virus can be isolated from humans and chimpanzees. Blood is infectious and if a person in this window donates blood, the antibody assays would score negative but the blood could transmit infectious virus. Thus, this method can be used to detect HIV in the blood supply.

A further embodiment of the instant invention relates to a method for monitoring the progression of HIV infection in a human. The level of the p7 marker is measurable in most asymptomatic subjects and identifies most of the individuals who will rapidly progress to AIDS. In contrast, the CD4 cell count and p24 antigen status does not fulfill these requirements. Further, other than CD4 counts, most other surrogate markers do not allow identification of the HIV-1 infected individuals that will rapidly progress to AIDS. Plasma viremia has been associated with onset of disease and a drop in CD4+cells; plasma viremia and absence of anti-p24 antibodies have been the most reliable virologic markers for AIDS disease progression. Further, viremia appears to be present throughout infection with HIV with a definite increase before the person progresses to AIDS.

Thus, the instant invention provides a needed method to or the like monitor the progression of HIV. A lysate of a biological sample such as a plasma sample or serum sample obtained from the human is contacted with a detectable amount of an antibody specifically reactive with the p7 antigen or an immunoreactive fragment of the p7 antigen for a time and under conditions sufficient for p7 antigen contained in the lysate to form a p7-antibody complex. The concentration of the p7-antibody complex in the lysate is determined a multiplicity of times over a period of time, thereby detecting the concentration of p7 in the plasma or serum of the human over this period of time. For instance, biological samples can be obtained at least two times up to as many times as desired during the time the progression of HIV is being monitored. The period of time between obtaining successive samples can be chosen as desired, such as from approximately one day to a year or more between samples, preferably from about one week to about two months between samples. An increase of the concentration of p7 in the plasma or serum correlates with increased progression of HIV infection. For example, a definite increase in the concentration of p7 in the plasma or serum of the human indicates the transition from asymptomatic HIV infection to the development of AIDS.

A still further embodiment of the instant invention includes a method for evaluating the effectiveness of an anti-HIV treatment administered to an animal (including humans). Anti-HIV-1 activity of AZT can be demonstrated as early as 4 weeks post treatment by marked decrease in the level of plasma viremia. Thus, the level of p7 should be specifically altered by the effectiveness of the treatment. The method of the instant invention involves obtaining a lysate of a plasma sample or serum sample or the like from the animal and contacting it with a detectable amount of an antibody specifically reactive with the p7 antigen or an immunoreactive fragment of the p7 antigen for a time and under conditions sufficient for p7 antigen contained in the lysate to form a p7-antibody complex. Thus, the concentration of the p7-antibody complex in the lysate is determined, which leads to the concentration of p7 in the plasma or serum of the animal. This procedure is repeated a multiplicity of times over a preselected period of time, similar to the procedure for monitoring HIV progression discussed above. A decrease of the concentration of p7 in the plasma or serum correlates with a decreased level of plasma viremia or serum viremia. This method can be used to screen potential anti-HIV treatments for effectiveness or to monitor the course of an approved anti-HIV treatment so as to determine its appropriateness for the animal.

Detecting the reaction of the antibody (or ligand) with the antigen can be facilitated by the use of an antibody or ligand that is labeled with a detectable moiety by methods known in the art. Such a detectable moiety will allow visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-strepavidin (for light or electron microscopy) and alkaline phosphatase (for biochemical detection by color change). The detection methods and moieties used can be selected, for example, from the list above or other suitable examples by the standard criteria applied to such selections (Harlow and Lane, *Antibodies: A Laboratory Manual*, Cold Spring Harbor Laboratory, Cold Spring Harbor, N.Y., 1988).

In the present invention, detecting the reaction of the ligand with the antigen can be further aided, in appropriate instances, by the use of a secondary antibody or other ligand which is reactive, either specifically with a different epitope or nonspecifically with the ligand or reacted antibody.

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a biological sample, such as a bodily fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change.

The present invention is more particularly described in the following examples which are intended as illustrative only since numerous modifications and variations therein will be apparent to those skilled in the art.

EXAMPLE 1

Purification of p7

HIV-1 p7 from strain MN was purified according to Henderson et al, *J. Vir.*, 66:1856–1865 (1992). In short, H9 cells chronically infected with HIV-1$_{MN}$ were grown in roller bottles under biosafety level 3 laboratory conditions. Virus production was increased approximately 50-fold by supplementing infected H9 cells with an equal number of uninfected H9 cells after each harvest. Virus was harvested from the culture medium every 3 to 4 days, isolated by continuous-flow sucrose density centrifugation, and further concentrated by ultracentrifugation (1000,000×g). Concentrated virus was resuspended in 0.01M Tris hydrochloride (pH 7.2)/0.1M NaCl/1.0 mM EDTA to a final protein concentration of 8 to 20 mg/m. and stored frozen at −70° C.

The concentrated virus was disrupted and reduced under biosafety level 3 conditions by adding solid guanidine hydrochloride (Pierce, Rockford, Ill.) to suspensions of concentrated virus (1.53 g/ml of virus suspension) to yield a final concentration of 0.76 g/ml (saturated at room temperature). The pH was adjusted to 8.5 by the addition of concentrated Tris hydrochloride buffer, and 2-mercaptoethanol was added to a final concentration of 2% (v/v). The resulting clear solution was transferred to a clean sterile tube and removed from the biosafety level 3 environment.

The protein and peptides were purified by preparative reverse-phase high-pressure liquid chromatography (rp-HPLC). All samples for rp-HPLC were dissolved in saturate guanidine hydrochloride containing 2% 2-mercaptoethanol at pH 8.5 and sonicated at 50° C. for 15 minutes before injection into the chromatographic column. Separations were performed an a µBondapak C18 (Waters Associates, Medford, Mass.) rp-HPLC supports by use of a liquid chromatograph (Pharmacia LKB, Piscataway, N.J.) equipped with a rapid spectral detector (model 2140). Elutions were accomplished with 0.05% (v/v) trifluoroacetic acid at pH 2 and with a gradient of increasing acetonitrile concentrations. Eluted proteins and peptides were detected UV absorption at 206, 280, and 294 nm and collected, and the solvents were removed by lyophilization. UV peaks associated with purified viral proteins p2, p7, p1, p6, p17 (group of partly separated peaks a–e) and p24 were separated from each other using this procedure.

The purified p7 has been extensively analyzed and results from amino acid sequencing and nuclear magnetic resonance analysis have been published [Summers et al, *Protein Science*, 1:563–574 (1992)]. The HIV-1 p7 contains two zinc fingers that specifically recognize and package the viral RNA genome [Gorelick et al., *J. Vir.*, 64:3207–3211 (1990)]. Since this protein requires zinc to form the fingers in the appropriate structure for oligonucleotide binding, care was taken to assure that the protein used in the studies described below was properly associated with zinc. A Coomassie stained SDS-PAGE of the purified p7 used as the antigen in assay development and to generate antisera is shown in FIG. 1.

EXAMPLE 2

Production of Antisera and Antibodies

Rabbits were inoculated with 2 ml of complete Freund's adjuvant containing 50 ug of p7. Subsequent inoculations were in incomplete Freund's adjuvant containing 50 ug and the boosts were monthly. Goats were immunized with 100 ug of p7 in complete Freund's adjuvant and boosts consisted of 50 ug of p7 in incomplete Freund's adjuvant at monthly boosts.

EXAMPLE 3

Serological Screening for Anti-p7

An ELISA to detect antibodies for p7 was developed using (1) a carbonate/bicarbonate buffer (pH 10.0) as the coating buffer [carbonate 0.05M solution in ddH$_2$O, bicarbonate 0.05M solution in ddH$_2$O, pH adjusted by adding carbonate to bicarbonate solution]; (2) 5% BSA buffer as blocking, conjugate and sample diluents [30% BSA stock solution (Sigma Chemical Co., St. Louis Mo.) diluted in PBS to make the 5% BSA buffer]; (3) a wash buffer from HTLV-1 p21E recombinant EIA kit (Cambridge Biotech, Worchester, Mass.) as the wash solution; (4) non sterile 96-well flat-bottom plates (Nunc Naperville, Ill.); (5) goat anti-human IgG-AP (Boehringer Mannheim Indianapolis, Ind.) and anti-sheep/goat IgG-AP, Fab fragments (Boehringer Manneheim Indianapolis, Ind.) as conjugates; (6) a diethanolamine substrate buffer (10%; pH 9.8) formed by combining 800 ml ddH$_2$O, 97 ml diethanolamine, 0.2 g NaN$_3$, and 100 mg MgCl-6H$_2$O; (7) a para-nitrophenylphosphate substrate solution (1 mg/ml) formed by dissolving PNP tablets (Sigma Chemical Co., St. Louis, Mo.) in diethanolamine buffer @ 1 tablet/5 ml 15–20 minutes prior to use; (8) 3N NaOH stop solution; and (9) normal human AB serum (Sigma Chemical Co., St. Louis, Mo.).

The plates were washed with wash solution on an automatic plate washer (Skatron Microwash®2, Lier, Norway) five times using at least 350 µl of fluid per well and tapped dry on paper towels. The plates were blocked with 300 µl per well of blocking solution and covered with a plate sealer. Following incubation at 37° C. for at least 2½ hours, the plates were washed again as before. The serum and controls were diluted 1:20 in sample diluent, 100 µl were added to proper the wells on the ELISA plate, and the plate was covered with a plate sealer and incubated for 1 hour at 37° C. After washing the plate again as before, goat anti-human IgG-AP was diluted @ 1–3000 in conjugate buffer for human samples and Anti-sheep/goat IgG-AP, Fab fragments were diluted @ 1–800 in conjugate buffer for goat positive and negative controls. 100 µl of conjugate were added to the appropriate wells and the plates were covered with a plate sealer and incubated for ½ hour at 37° C. 50 µl of stop solution were added to each well and the plates were read at 405 nm in an automated ELISA plate reader (BIO-TEK® Model EL312e, Winooski, Vt.).

Antisera prepared in animals by immunization with purified p7 and sera from HIV-1 positive humans were screened using this assay. Anti-p7 sera from goats and rabbits scored positive with titers of greater than 180,000 and 100,000, respectively. However, no samples scored positive for antibodies to p7 out of 43 HIV-1 positive human samples tested with this assay. Apparently, in the context of an active infection, the p7 of HIV-1 is not an effective immunogen. Most likely, because p7 is immunoreactive, the antibody production machinery is not exposed to p7, which is an interior core protein and tightly bound to RNA.

EXAMPLE 4 p7 Antigen Capture Assay

A p7 capture assay was constructed utilizing immunoglobulin from either a goat or rabbit, preferably a goat, immunized with p7. The immunoglobulins from the sera were enriched by $(NH_4)_2SO_4$ precipitation and this enriched immunoglobulin was used to coat the plate according to standard procedures. After blocking the plate, a solution containing p7 (i.e., purified p7, lysed HIV-1, plasma, etc.) is added and the p7 is bound by the immobilized anti-p7. After washing, rabbit anti-p7 is added and the rabbit immunoglobulin binds to the immobilized p7. Unbound rabbit immunoglobulin is removed by washing and an ELISA format is used to detect the rabbit immunoglobulin bound to the p7. For instance, antisera against rabbit IgG that has been conjugated to biotin is added, which binds to the immobilized rabbit anti-p7. After washing, alkaline phosphatase conjugated to strepavidin is added. The strepavidin on this conjugate binds to the biotin on the anti-rabbit IgG conjugate and this complex is detected by adding ELISA Amplification System (GIBCO BRL Life Technologies, Inc., Gaithersburg, Md.), which contains a substrate that is catalyzed to a product by the alkaline phosphatase bound to the strepavidin.

This capture assay allows the detection of p7 antigen in biological samples containing p7, including body fluids, such as serum or plasma, tissues, cell culture fluid and the like. Typically, the biological sample is treated by methods known to one skilled in the art to lyse the cells present in the biological sample.

One embodiment of the method for detecting p7 antigen is performed by contacting the lysate of a biological sample, such as a bodily fluid or tissue sample from a subject, with a detectable amount of a purified antibody specifically reactive with the p7 or an immunoreactive fragment of p7 and detecting the reaction of the antibody with the antigen. For instance, a detergent-treated serum sample is added to the immobilized antibody that is specifically reactive with p7, allowing the p7 antibody to bind to the p7 from the lysed virus, if present. Excess unbound p7 antibody is washed off and the p7 bound to the immobilized antibody is detected by use of another antibody to p7, which is attached to a secondary system that allows for detection.

Another embodiment incorporates the use of at least one monoclonal antibody. The selection of the appropriate monoclonal antibody to p7 can significantly enhance the sensitivity and specificity of the assay because the monoclonal is directed to only one epitope on the p7 molecule. If a monoclonal rather than a polyclonal is used as the capture, only one epitope on the p7 is bound, leaving the rest of the epitopes free to react with the detector antibody. In contrast, an assay that uses polyclonal antibody as the capture agent conceivably binds many epitopes, making them unavailable for reaction with the detector antibody.

Typically, the p7 assay of this invention is capable of detecting the presence of approximately 1 pg–200 pg, preferably 1 pg–50 pg virus/ml of sample. The detection can be enhanced, however, to allow detection of approximately 500–1000 molecules or less by use of the recently published Immuno-PCR (*Science*, 258:120 (1992)), which can detect as few as 580 antigen molecules. The Immuno-PCR technique can be modified to allow the PCR product to be detected in the well of the 96-well plate rather than by agarose gel electrophoresis and ethidium bromide staining.

EXAMPLE 5

Detection of HIV-1 in Serum by p24 and p7 Antigen Capture Assays

In a reconstruction experiment to evaluate methods for detecting HIV-1 in serum, various quantities, approximately 10 pg to 10,000 pg, of sucrose gradient purified HIV-1 was added to normal (NHS) and HIV-1 antibody positive human sera (A4461, A4311 and A4313). Antigen capture assays for p7 (as described in Example 4) and p24 (HIV p24 Core Antigen Capture Assay, Du Pont, Boston, Mass.) were then used to quantitatively detect virus in the serum. The p24 capture assays were conducted according to manufacturer's instructions.

Figure 2:
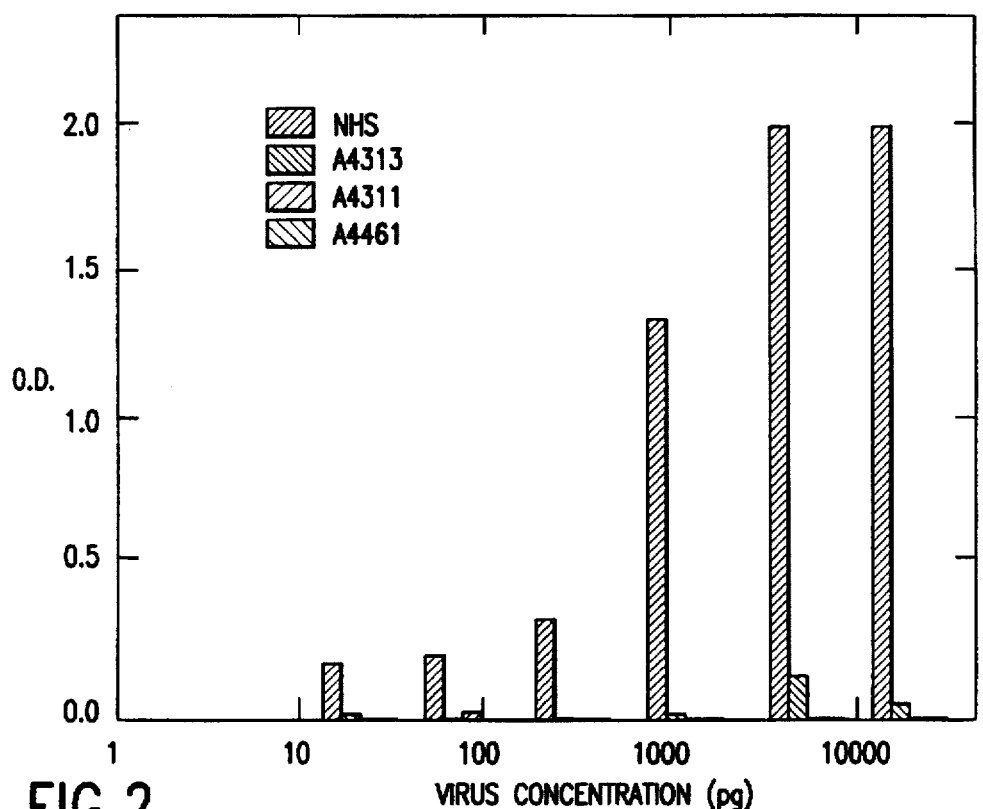
FIG. 2 shows the results obtained from testing sera that have been spiked with approximately 10 pg to 10,000 pg of sucrose gradient purified HIV-1 in a conventional p24 antigen capture assay. The optical density values versus spiked virus concentration for uninfected normal human sera (NHS) and HIV-1 antibody positive human sera (A4461, A4311 and A4313) are shown.
Figure 3:
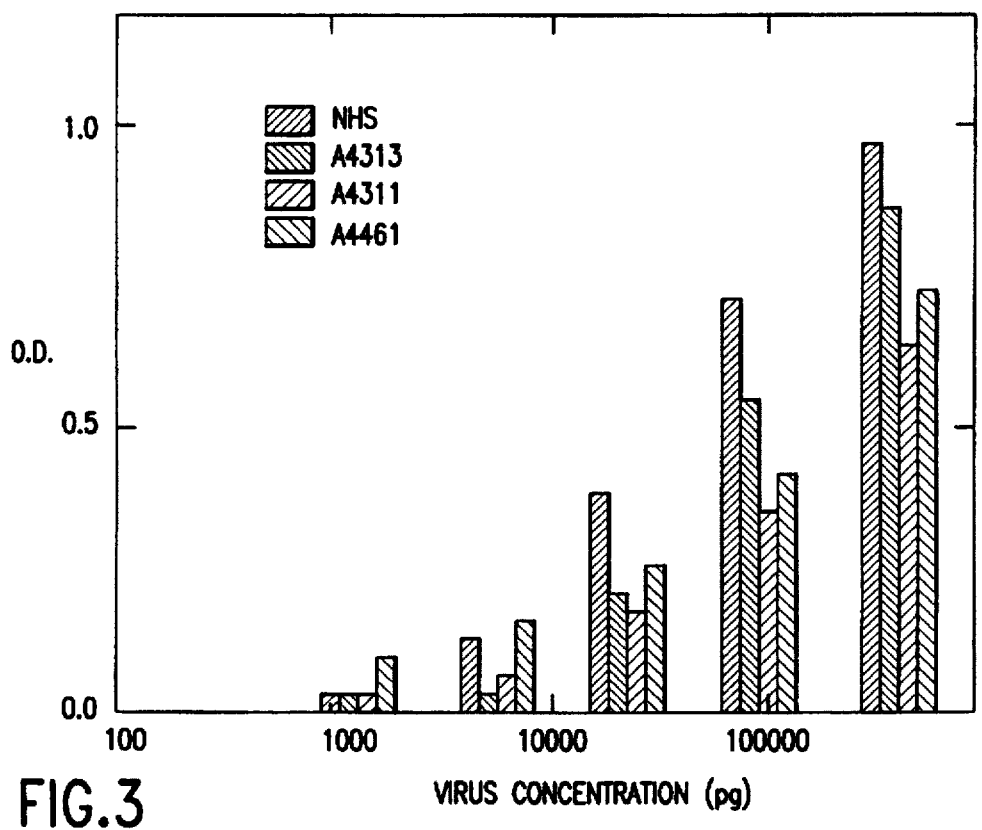
FIG. 3 shows the results obtained from testing sera that have been spiked with approximately 100 pg to 100,000 pg of sucrose gradient purified HIV-1 in one embodiment of the antigen capture assay of this invention. The optical density values versus spiked virus concentration for uninfected normal human sera (NHS) and HIV-1 antibody positive human sera (A4461, A4311 and A4313) are shown.

As shown in FIG. 2, virus was readily detected by the p24 antigen capture assay in the normal human sera at concentrations as low as 10 pg virus/ml of serum. However, this assay was ineffective in detecting the presence of HIV-1 in HIV-1 positive sera. At concentrations of virus greater than 10,000 pg of virus/ml, the p24 assay scored negative in the HIV-1 antibody positive sera, presumably due to the immune complexes formed with anti-p24 antibodies in the sera and the p24 which is released from the virus by detergent treatment. In contrast, the p7 capture assay detected virus efficiently in both normal serum as well as in HIV-1 positive sera as shown in FIG. 3. In normal human serum, the p7 capture assay is 100-fold less sensitive that the p24 capture assay. However, if virus is resuspended in sera containing antibodies to HIV-1, the sensitivity of this p7 capture assay is more than 10-fold more sensitive than the p24 capture assay.

Given the antigen capture assay of this invention, one skilled in the art can readily determine the amount of virus present in biological samples taken from an infected individual over the course of infection. In this way, one skilled in the art can determine the expected values for a particular antigen capture assay for non-infected samples as well as the various stages of infection for infected samples. Further, methods to normalize the values from a particular antigen capture assay can be determined to allow routine use of the assay as described herein.

Although the present process has been described with reference to specific details of certain embodiments thereof, it is not intended that such details should be regarded as limitations upon the scope of the invention except as and to the extent that they are included in the accompanying claims.

What is claimed is:

1. An antigen capture method for detecting the presence of a lentivirus in a biological sample, comprising the steps of:

a) contacting a lysate of the biological sample with a detectable amount of an antibody specifically reactive with the nucleocapsid protein of the lentivirus or with an immunoreactive fragment of the nucleocapsid protein for a time and under conditions sufficient for nucleocapsid protein contained in the lysate to form a nucleocapsid protein-antibody complex; and b) determining the presence of the nucleocapsid protein-antibody complex, thereby detecting the presence of the lentivirus in the biological sample.

2. The antigen capture method of claim 1, wherein the lentivirus is selected from the group consisting of HIV-1, HIV-2, SIV, bovine immunodeficiency virus, feline immunodeficiency virus, equine infectious anemia virus, caprine arthritis encephalitis virus and visna virus.

3. A purified antibody specifically reactive with an immunoreactive epitope specific to a nucleocapsid protein of a lentivirus or with an immunoreactive fragment of the nucleocapsid protein of a lentivirus.

4. The method of claim 1, further comprising quantitating the amount of nucleocapsid protein-antibody complex to determine the extent of lentivirus viremia in the biological sample.

5. The method of claim 1, wherein the antibody specifically reactive with the nucleocapsid protein antigen or with an immunoreactive fragment of the nucleocapsid protein antigen is immobilized and the determining step comprises the steps of:

a. removing excess antibody that is not bound to nucleocapsid protein;

b. contacting the nucleocapsid protein-antibody complex with a secondary antibody that is labeled with a detectable moiety, wherein the secondary antibody is capable of binding with the nucleocapsid protein-antibody complex; and c. measuring the presence of the secondary antibody bound to the nucleocapsid protein-antibody complex to detect the presence of lentivirus in the biological sample.

6. The method of claim 5, further comprising quantitating the amount of secondary antibody bound to the nucleocapsid protein-antibody complex to determine the extent of lentivirus viremia in the biological sample.

7. The method of claim 1, wherein the biological sample is selected from the group consisting of a bodily fluid, tissue, or cell culture fluid.

8. The method of claim 1, wherein the biological sample is selected from the group consisting of blood, serum, plasma, saliva and urine.

9. The antibody of claim 3, wherein the antibody is labeled with a detectable moiety.

10. The antibody of claim 3, wherein the antibody is bound to a solid support.

11. A method for monitoring the level of lentivirus viremia progression of lentivirus infection in an animal, comprising the steps of:

a. at a multiplicity of times spaced over a period of time, obtaining a biological sample from an animal;

b. for each biological sample, contacting a lysate of the biological sample with a detectable amount of an antibody specifically reactive with a lentivirus nucleocapsid protein antigen or with an immunoreactive fragment of a lentivirus nucleocapsid protein antigen for a time and under conditions sufficient for the nucleocapsid protein antigen contained in the lysate to form a nucleocapsid protein-antibody complex;

c. determining the concentration of the nucleocapsid protein-antibody complex in the lysate, thereby determining the concentration of nucleocapsid protein in the biological sample; and d. comparing the concentration of nucleocapsid protein in the biological samples obtained over the period of time, wherein an increase of the concentration of nucleocapsid protein over the period of time correlates with increased level of lentivirus viremia and a decrease of the concentration of nucleocapsid protein over the period of time correlates with decreased level of lentivirus viremia.

12. An antigen capture assay diagnostic kit for the detection of the presence or amount of a lentivirus nucleocapsid protein, comprising:

a. an antibody specifically reactive with a lentivirus nucleocapsid protein antigen or with an immunoreactive fragment of a lentivirus nucleocapsid protein antigen; and b. means for detecting the formation of immune complexes between the nucleocapsid protein and the antibody specifically reactive with the nucleocapsid protein antigen or an immunoreactive fragment of the nucleocapsid protein antigen.

13. The diagnostic kit of claim 12, wherein the means for detecting the formation of the immune complexes comprise a reagent for ascertaining the presence of an antibody labeled with a detectable moiety.

* * * * *

UNITED STATES PATENT AND TRADEMARK OFFICE
CERTIFICATE OF CORRECTION

PATENT NO. : 5,705,331
DATED : January 6, 1998
INVENTOR(S) : Larry O. Arthur et al.

It is certified that error appears in the above-identified patent and that said Letters Patent is hereby corrected as shown below:

On the cover page, item [*], please delete: "Notice: The portion of the term of this patent subsequent to October 31, 2002, has been disclaimed."
Please substitute therefor:
--Notice: The portion of the term of this patent subsequent to October 31, 2012, has been disclaimed.--

Signed and Sealed this

Seventeenth Day of November, 1998

Attest:

BRUCE LEHMAN

Attesting Officer

Commissioner of Patents and Trademarks